(12) United States Patent
Yang et al.

(10) Patent No.: US 8,153,092 B2
(45) Date of Patent: *Apr. 10, 2012

(54) METHOD FOR MANUFACTURING HYDROXYLAMINE

(75) Inventors: Shu-Hung Yang, Taipei (TW); Cheng-Fa Hsieh, Taipei (TW); Yi-Bau Hung, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/053,774

(22) Filed: Mar. 22, 2011

(65) Prior Publication Data

US 2011/0171103 A1 Jul. 14, 2011

Related U.S. Application Data

(60) Continuation-in-part of application No. 12/459,784, filed on Jul. 8, 2009, which is a division of application No. 11/784,273, filed on Apr. 5, 2007, now Pat. No. 7,892,512.

(30) Foreign Application Priority Data

Apr. 14, 2006 (TW) ............................... 95113373 A

(51) Int. Cl.
*C01B 21/14* (2006.01)
(52) U.S. Cl. ..................................... 423/387
(58) Field of Classification Search ............ 210/660, 210/663, 665, 668, 681, 688, 702, 704, 705, 210/722, 723, 749, 757, 758; 423/302, 387; 502/185, 325, 326, 339; 564/259, 264
See application file for complete search history.

(56) References Cited

U.S. PATENT DOCUMENTS

| | | |
|---|---|---|
| 3,514,254 A | 5/1970 | de Rooij |
| 3,720,755 A | 3/1973 | Duyverman et al. |
| 3,767,758 A | 10/1973 | Mars et al. |
| 3,940,442 A | 2/1976 | de Rooij |
| 4,062,927 A | 12/1977 | De Rooij et al. |
| 4,111,842 A | 9/1978 | van Montfoort et al. |
| 4,158,047 A | 6/1979 | van de Moesdijk et al. |
| 4,340,575 A | 7/1982 | Rapp et al. |
| 4,956,168 A | 9/1990 | Wagaman |
| 7,491,846 B2 | 2/2009 | Aoki et al. |

FOREIGN PATENT DOCUMENTS

WO 98/18717 A1 5/1998

*Primary Examiner* — Emily Le
*Assistant Examiner* — Brittany Martinez
(74) *Attorney, Agent, or Firm* — Peter F. Corless; Dwight D. Kim; Edwards Wildman Palmer LLP

(57) ABSTRACT

Provided is a method for manufacturing hydroxylamine. In this method, an aqueous reaction medium containing acidic buffer agent and nitrate ions in the presence of a limited amount of metal impurities such as Fe is introduced into a hydroxylamine synthesis reactor in the presence of catalyst to proceed hydroxylamine synthesis by reduction of nitrate ions with hydrogen gas as reducing agent in the aqueous reaction medium to produce hydroxylamine. The reaction is processed in the aqueous reaction medium with a limited amount of metal impurities, such that the selection rate of the hydroxylamine product is increased while high catalytic activity is kept.

11 Claims, No Drawings

METHOD FOR MANUFACTURING HYDROXYLAMINE

RELATED APPLICATIONS

This application is a continuation in part of U.S. Ser. No. 12/459,784, filed on Jul. 8, 2009, which is a divisional application of U.S. Ser. No. 11/784,273 (now U.S. Pat. No. 7,892,512), filed on Apr. 5, 2007, which claims the benefit of Taiwan 095113373, filed on Apr. 14, 2006. The contents of each of the above-referenced applications and patents is incorporated herein in its entirety by reference.

BACKGROUND OF THE INVENTION

1. Field of the Invention

The present invention relates to a method for manufacturing hydroxylamine, particularly a method using hydrogen gas as reducing agent to reduce the nitrate ions to produce hydroxylamine.

2. Description of Related Art

Hydroxylamine related manufacturing steps are generally combined with other manufacturing steps to constitute a recycling system in the industrial application, for example, hydroxylamine—oximation recycling system, i.e., using phosphate salt as an aqueous reaction medium, and using nitric acid, hydrogen gas as raw materials in a catalytic reaction to reduce nitrate ions to hydroxylamine, followed by adding cyclohexanone to the produced hydroxylamine to proceed the oximation reaction to form cyclohexanone oxime. After the foregoing oximation reaction, the resultant reaction mixture was supplemented with nitric acid or subjected to adsorption of nitrous gas to generate nitric acid in order to increase the required amount of nitrate ions, which were consequently transferred into a hydroxylamine reactor for the hydroxylamine synthesis. The reactions could be shown as follows:

Reaction of Hydroxylamine to Produce Hydroxylamine Phosphate

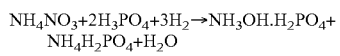

$NH_4NO_3 + 2H_3PO_4 + 3H_2 \rightarrow NH_3OH \cdot H_2PO_4 + NH_4H_2PO_4 + H_2O$ Oximation Reaction to Produce Cyclohexanone Oxime

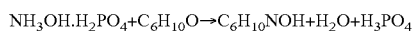

$NH_3OH \cdot H_2PO_4 + C_6H_{10}O \rightarrow C_6H_{10}NOH + H_2O + H_3PO_4$

Supplementation of Nitrate Ion to the Inorganic Phosphate Manufacturing Solution.

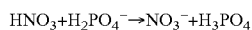

$HNO_3 + H_2PO_4^- \rightarrow NO_3^- + H_3PO_4$

During the manufacturing process, the aqueous reaction medium was recycled through the hydroxylamine reaction zone and the cyclohexanone oxime synthesizing zone. The content and the quality level of the reaction medium directly affected the efficiency of the hydroxylamine production. U.S. Pat. No. 3,767,758 discloses that the aqueous reaction medium containing metals such as Mo, Rh and Ru declines the selection rate of the hydroxylamine production. U.S. Pat. No. 4,062,927 discloses that acidic solution corrupts the equipments and devices to increase the amount of heavy metal contamination in aqueous reaction medium, particularly, the generated Mo metal contamination may decline the selection rate by 5 to 15%. Said patent teaches the using of ferric ammonium phosphate as a precipitant to remove the metal ions in the reaction medium by co-precipitation. However, the selection rate of the hydroxylamine production is still lower than 87% according to the disclosure of said patents.

Therefore, a method in which the process is simple and effectively increasing the selection rate of the hydroxylamine production while maintaining high catalytic activity is indeed required.

SUMMARY OF THE INVENTION

It is an object of the present invention to provide a method for manufacturing hydroxylamine with high selection rate.

It is another object of the present invention to provide a method for manufacturing hydroxylamine with high catalytic activity.

In order to achieve the aforesaid and other purposes, the present invention provides a method for manufacturing hydroxylamine. The present method is carried in an aqueous reaction medium containing acidic buffer agents and nitrate ions in the presence of little metal impurities such as Fe in the presence of catalyst and utilize hydrogen gas as the reducing agent to reduce nitrate ions to hydroxylamine. The method of the present invention uses the aqueous reactive medium containing low amount of metal impurities to process hydroxylamine synthesis reaction in order to increase the selection rate of hydroxylamine production while maintaining high catalytic activity.

EXAMPLES

The present invention is further explained by using exemplified embodiments to clarify the characteristics and effects of the present invention.

The method of the present invention is carried out in an aqueous reaction medium containing acidic buffer agents such as sulfuric acid, phosphoric acid or salts thereof, and nitrate ions with little metal impurities, in the presence of catalyst by reducing hydroxylamine with hydrogen gas as the reducing agent to reduce nitrate ions to hydroxylamine. This method can elevate the selection rate of hydroxylamine production while maintaining high catalytic activity by lowering the amount of metal impurities in the aqueous reaction medium. In the present invention, the selection rate of hydroxylamine production is defined as follows:

selection rate of hydroxylamine production=2 times hydroxylamine yield/amount of hydrogen ion consumption×100%.

In one embodiment, the method of the present invention provides an inorganic phosphate solution used as the aqueous manufacturing reaction medium to synthesize hydroxylamine phosphate. The components of the aqueous reaction medium include phosphate ion, ammonium ion, nitrate ion and metal impurities such as Fe, Mo, Ni, Bi, Co, Cu, Mn, Sn, W and Zn etc. In order to prevent the decrease of the selection rate of hydroxylamine production caused by the metal impurities in the aqueous reaction medium. This embodiment illustrates that the aqueous reaction medium (such as an aqueous reaction medium taken from an oximation reaction of a hydroxylamine-oxime cycling process) was pretreated for the purpose of lowering the amount of the metal impurities therein, particularly, the amount of Fe metal impurity, and then was introduced into the hydroxylamine synthesizing zone to proceed the hydroxylamine synthesis reaction. The pretreatment can be carried by, but not limited to, for example, adding precipitant to react with metal impurities to form precipitated metal complexes which are removed thereafter, or by utilizing resin to adsorb the metal impurities, or by any appropriate methods that can decrease or remove the metal impurities.

According to the method of the present invention, in the hydroxylamine synthesis reactor, the amount of metal impurities such as Fe in the aqueous medium (after pretreatment) is preferably less than 100 ppm, more preferably less than 75 ppm, still preferably less than 55 ppm or below, further preferably less than 30 ppm. The selective rate of hydroxylamine production is preferably higher than 87%, more preferably higher than 90%, still preferably higher than 91.5%, further preferably higher than 94% or above. On the other hand, in the context of catalytic activity, the content of the metal impurity, Fe, in the aqueous reaction medium (after pretreatment) for hydroxylamine reaction in the hydroxylamine synthesis reactor is preferably at 10 ppm or more, 15 ppm or more or 20 ppm or more, so as to maintain the catalytic activity of catalysts (e.g., Pd/C catalyst) capable of participating in the hydroxylamine reaction at 20 g hyam/g metal-hr or higher, preferably at 23 g hyam/g metal-hr or higher, and more preferably at 24 g hyam/g metal-hr or higher. Preferably, in the method of the present invention, the Fe content of the aqueous reaction medium for hydroxylamine reaction in the hydroxylamine synthesis reactor is between 10 to 100 ppm, and more preferably between 10 to 75 ppm, between 15 to 55 ppm, between 15 to 50 ppm, between 15 to 30 ppm or between 20 to 30 ppm.

In a preferred embodiment, the reaction step is performed by utilizing phosphate inorganic manufacturing solution in the hydroxylamine-oximation recycling system as the aqueous reaction medium for manufacturing hydroxylamine phosphate. The aqueous reactive medium may be pretreated to remove the metal impurities such as Fe. The reaction step is previously supplemented with nitrate ions before the operation of hydroxylamine synthesis. Based on the total weight of aqueous reactive medium, the amount of nitrate ion in the acidic buffer agent is preferably 13 to 18% by weight, more preferably 14 to 16.5% by weight. In the method of the present invention, the reaction condition for processing the hydroxylamine synthesis in the hydroxylamine synthesis reactor is not particularly limited. The reaction conditions generally used for the reduction of nitrate ions through the addition of hydrogen gas as reducing agent would be suitable. For example, it may be performed preferably at a temperature of 20 to 100° C., more preferably 30 to 90° C.; and preferably under a pressure of 10 to 30 kg/cm$^2$, more preferably 18 to 26 kg/cm$^2$, still preferably 18 to 24 kg/cm$^2$; preferably at pH of 0.5 to 6, more preferably 1 to 3.5. As to the constitution of the entering gas for hydroxylamine reaction, based on the total amount of hydrogen gas and nitrogen gas, the content of hydrogen gas is preferably in the range of 30 to 70%, more preferably in the range of 45 to 55%. The catalyst used in the hydroxylamine reaction includes, but not limited to, the noble metal catalyst containing Pd, or Pd—Pt. The carrier for catalyst includes, but not limited to, carbon or aluminum oxide. In general, based on the total weight of catalyst carrier and catalyst, the amount of the noble metal catalyst is preferably in the range of 1 to 25% by weight, more preferably in the range of 5 to 15% by weight. The amount of catalyst used in the hydroxylamine reaction, based on the total amount of the acidic buffer solution, is usually in the range of 0.2 to 5% by weight.

The method of the present invention is performed by utilizing aqueous reaction medium with low metal impurities, in which the content of Fe is particularly below 100 ppm, so that the selective rate of hydroxylamine product is elevated to more than 87%, or even more than 90%, even to 94% or above. Further, the method of the present invention is performed by utilizing aqueous reaction medium with low metal impurities, in which the content of Fe is between 10 to 100 ppm, so that yield of hydroxylamine is increased by increasing the selection rate of hydroxylamine production while maintaining high catalytic activity.

The invention is further illustrated by the following examples in detail for clarifying the characteristics and effectiveness of the present invention. The detailed embodiments are merely used for clarifying the characteristics of the present invention. The present invention is not limited to the particular embodiment illustrated.

Example 1

The aqueous reaction medium, hydrogen gas and nitrogen gas were introduced into the hydroxylamine synthesizing zone. The hydroxylamine synthesis in the presence of Pd—Pt catalyst, at the temperature of 50° C. under the pressure of 24 kg/cm$^2$. The Fe metal content was analyzed by induced coupled plasma-optical emission spectrometry (ICP-OES) to give a result of Fe content of 98 ppm. The selection rate of hydroxylamine production was 87.20%. Based on the total amount of the aqueous reaction medium, the components of the hydroxylamine reaction medium introduced into the hydroxylamine synthesizing zone were as follows:
[$H^+$] 0.292% by weight
[$H_2PO_4^-$] 20.13% by weight
[$NH_4^+$] 4.17% by weight
[$NH_3OH^+$] 0.082% by weight
[$NO_3^-$] 15.7% by weight Example 2

The aqueous reaction medium, hydrogen gas and nitrogen gas were introduced into the hydroxylamine synthesizing zone. The hydroxylamine synthesis was carried out in the of Pd—Pt catalyst, at the temperature of 50° C. under the pressure of 24 kg/cm$^2$. The Fe metal content was analyzed by induced coupled plasma-optical emission spectrometry (ICP-OES) to give a result of Fe content of 91 ppm. The selection rate of hydroxylamine production was 88.50%. Based on the total amount of the aqueous reaction medium, the components of the hydroxylamine reactive medium introduced into the hydroxylamine synthesizing zone were as follows:
[$H^+$] 0.305% by weight
[$H_2PO_4^-$] 20.17% by weight
[$NH_4^+$] 4.14% by weight
[$NH_3OH^+$] 0.077% by weight
[$NO_3^-$] 16.2% by weight Example 3

The aqueous reaction medium, hydrogen gas and nitrogen gas were introduced into the hydroxylamine synthesizing zone. The hydroxylamine synthesis was carried out in the presence of Pd—Pt catalyst, at the temperature of 50° C. under the pressure of 24 kg/cm$^2$. The Fe metal content was analyzed by induced coupled plasma-optical emission spectrometry (ICP-OES) to give a result of Fe metal content of 85 ppm. The selection rate of hydroxylamine production was 89.21%. Based on the total amount of the aqueous reaction medium, the components of the hydroxylamine reaction medium introduced into the hydroxylamine synthesizing zone were as follows:
[$H^+$] 0.297% by weight
[$H_2PO_4^-$] 20.13% by weight
[$NH_4^+$] 4.14% by weight
[$NH_3OH^+$] 0.078% by weight
[$NO_3^-$] 15.25% by weight

Example 4

The aqueous reaction medium, hydrogen gas and nitrogen gas were introduced into the hydroxylamine synthesizing zone. The hydroxylamine synthesis was carried out in the presence of Pd—Pt catalyst, at the temperature of 50° C. under the pressure of 24 kg/cm². The Fe metal content was analyzed by induced coupled plasma-optical emission spectrometry (ICP-OES) to give a result of Fe metal content of 72 ppm. The selection rate of hydroxylamine production was 90.50%. Based on the total amount of the aqueous reactive medium, the components of the hydroxylamine reaction medium introduced into the hydroxylamine synthesizing zone were as follows:
  [$H^+$] 0.298% by weight
  [$H_2PO_4^-$] 20.13% by weight
  [$NH_4^+$] 4.19% by weight
  [$NH_3OH^+$] 0.082% by weight
  [$NO_3^-$] 15.6% by weight

Example 5

The aqueous reaction medium, hydrogen gas and nitrogen gas were introduced into the hydroxylamine synthesizing zone. The hydroxylamine synthesis was carried out in the presence of Pd—Pt catalyst, at the temperature of 50° C. under the pressure of 24 kg/cm². The Fe metal content was analyzed by induced coupled plasma-optical emission spectrometry (ICP-OES) to give a result of Fe metal content of 34 ppm. The selection rate of hydroxylamine production was 91.50%. Based on the total amount of the aqueous reaction medium, the components of the hydroxylamine reaction medium introduced into the hydroxylamine synthesizing zone were as follows:
  [$H^+$] 0.301% by weight
  [$H_2PO_4^-$] 20.15% by weight
  [$NH_4^+$] 4.12% by weight
  [$NH_3OH^+$] 0.073% by weight
  [$NO_3^-$] 16.38% by weight

Example 6

The aqueous reaction medium, hydrogen gas and nitrogen gas were introduced into the hydroxylamine synthesizing zone. The hydroxylamine synthesis was carried out in the presence of Pd—Pt catalyst, at the temperature of 50° C. under the pressure of 24 kg/cm². The Fe metal content was analyzed by induced coupled plasma-optical emission spectrometry (ICP-OES) to give a result of Fe metal content of 25 ppm. The selection rate of hydroxylamine production was 94.20%. Based on the total amount of the aqueous reaction medium, the components of the hydroxylamine reaction medium introduced into the hydroxylamine synthesizing zone were as follows:
  [$H^+$] 0.304% by weight
  [$H_2PO_4^-$] 20.18% by weight
  [$NH_4^+$] 4.08% by weight
  [$NH_3OH^+$] 0.064% by weight
  [$NO_3^-$] 16.4% by weight

Comparative Example 1

The aqueous reaction medium, hydrogen gas and nitrogen gas were introduced into the hydroxylamine synthesizing zone. The hydroxylamine synthesis was carried out in the presence of Pd—Pt catalyst, at the temperature of 50° C. under the pressure of 24 kg/cm². The Fe metal content was analyzed by induced coupled plasma-optical emission spectrometry (ICP-OES) to give a result of Fe metal content of 116 ppm. The selection rate of hydroxylamine production was 85.21%. Based on the total amount of the aqueous reaction medium, the components of the hydroxylamine reaction medium introduced into the hydroxylamine synthesizing zone were as follows:
  [$H^+$] 0.290% by weight
  [$H_2PO_4^-$] 20.11% by weight
  [$NH_4^+$] 4.17% by weight
  [$NH_3OH^+$] 0.079% by weight
  [$NO_3^-$] 14.34% by weight

Comparative Example 2

The aqueous reaction medium, hydrogen gas and nitrogen gas were introduced into the hydroxylamine synthesizing zone. The hydroxylamine synthesis was carried out in the presence of Pd—Pt catalyst, at the temperature of 50° C. under the pressure of 24 kg/cm². The Fe metal content was analyzed by induced coupled plasma-optical emission spectrometry (ICP-OES) to give a result of Fe metal content of 105 ppm. The selection rate of hydroxylamine production was 86.80%. Based on the total amount of the aqueous reaction medium, the components of the hydroxylamine reaction medium introduced into the hydroxylamine synthesizing zone were as follows:
  [$H^+$] 0.293% by weight
  [$H_2PO_4^-$] 20.13% by weight
  [$NH_4^+$] 4.15% by weight
  [$NH_3OH^+$] 0.074% by weight
  [$NO_3^+$] 15.2% by weight

Comparative Example 3

The aqueous reaction medium, hydrogen gas and nitrogen gas were introduced into the hydroxylamine synthesizing zone. The hydroxylamine synthesis was carried out in the presence of Pd—Pt catalyst, at the temperature of 50° C. under the pressure of 24 kg/cm². The Fe metal content was analyzed by induced coupled plasma-optical emission spectrometry (ICP-OES) to give a result of Fe metal content of 143 ppm. The selection rate of hydroxylamine production was 84.35%. Based on the total amount of the aqueous reaction medium, the components of the hydroxylamine reaction medium introduced into the hydroxylamine synthesizing zone were as follows:
  [$H^+$] 0.295% by weight
  [$H_2PO_4^-$] 20.13% by weight
  [$NH_4^+$] 4.14% by weight
  [$NH_3OH^+$] 0.074% by weight
  [$NO_3^-$] 15.24% by weight Table 1 Shows the relationships between the Fe metal contents in the aqueous reaction medium and the selection rates of hydroxylamine production in the above examples.

TABLE 1

| | Fe Metal content (ppm) | Selection rate (%) |
|---|---|---|
| Example 1 | 98 | 87.20 |
| Example 2 | 91 | 88.50 |
| Example 3 | 85 | 89.21 |
| Example 4 | 72 | 90.50 |
| Example 5 | 34 | 91.50 |

TABLE 1-continued

|  | Fe Metal content (ppm) | Selection rate (%) |
|---|---|---|
| Example 6 | 25 | 94.20 |
| Comparative Example 1 | 116 | 85.21 |
| Comparative Example 2 | 105 | 86.80 |
| Comparative Example 3 | 143 | 84.35 |

Example 7

A standard buffer solution (as the aqueous reaction medium used in examples 1-6) with Fe content of 10 ppm was used as an aqueous reaction medium. The aqueous reaction medium was used to carry out a hydroxylamine synthesis reaction, along with hydrogen gas (50 l/hr) and nitrogen gas, in the presence of Pd/C catalyst (750 ppm, Pd 9.67, wt %) and $GeO_2$ (3.5 mg/g, catalyst), at the temperature of 50° C. and under the pressure of 24 $kg/cm^2$. The reaction lasted over 120 minutes. Samples were taken from the aqueous reaction medium at 30-minute intervals for analysis. As shown in Table 2, the catalytic activity was 24.6 g hyam/g metal-hr.

Example 8

The steps in example 7 were repeated, except that a standard buffer solution with Fe content of 20 ppm was used as an aqueous reaction medium for carrying out hydroxylamine synthesis reaction. The reaction lasted over 120 minutes. Samples were taken from the aqueous reaction medium at 30-minute intervals for analysis. As shown in Table 2, the catalytic activity was 26.3 g hyam/g metal-hr.

Example 9

The steps in example 7 were repeated, except that a standard buffer solution with Fe content of 30 ppm was used as an aqueous reaction medium for carrying out hydroxylamine synthesis reaction. The reaction lasted over 120 minutes. Samples were taken from the aqueous reaction medium at 30-minute intervals for analysis. As shown in Table 2, the catalytic activity was 23.9 g hyam/g metal-hr.

Example 10

The steps in example 7 were repeated, except that a standard buffer solution with Fe content of 50 ppm was used as an aqueous reaction medium for carrying out hydroxylamine synthesis reaction. The reaction lasted over 120 minutes. Samples were taken from the aqueous reaction medium at 30-minute intervals for analysis. As shown in Table 2, the catalytic activity was 24.1 g hyam/g metal-hr.

Comparative Example 4

The steps in example 7 were repeated, except that a standard buffer solution with Fe content of 5 ppm was used as an aqueous reaction medium for carrying out hydroxylamine synthesis reaction. The reaction lasted over 120 minutes. Samples were taken from the aqueous reaction medium at 30-minute intervals for analysis. As shown in Table 2, the catalytic activity was 19.1 g hyam/g metal-hr.

TABLE 2

|  |  | $H^+$ (mmole/l) | $NH_4^+$ (mmole/l) | $NH_2OH$ (mmole/l) |
|---|---|---|---|---|
| Example 7 | Blank | 924.4 | — | — |
|  | 30 min | 879.2 | 3.4 | 22.4 |
|  | 60 min | 818.0 | 2.6 | 38.7 |
|  | 90 min | 760.5 | 5.3 | 72.1 |
|  | 120 min | 702.7 | 2.0 | 98.8 |
| Example 8 | Blank | 935.6 | — | — |
|  | 30 min | 852.8 | 0.8 | 25.6 |
|  | 60 min | 801.8 | 2.0 | 47.4 |
|  | 90 min | 747.4 | 2.0 | 83.3 |
|  | 120 min | 685.5 | 3.2 | 112.0 |
| Example 9 | Blank | 928.0 | — | — |
|  | 30 min | 844.7 | 1.4 | 32.9 |
|  | 60 min | 773.5 | 1.0 | 64.2 |
|  | 90 min | 718.8 | 6.5 | 89.8 |
|  | 120 min | 646.9 | — | 122.4 |
| Example 10 | Blank | 923.7 | — | — |
|  | 30 min | 861.6 | 3.0 | 21.4 |
|  | 60 min | 800.0 | 1.8 | 54.7 |
|  | 90 min | 739.0 | 6.5 | 80.9 |
|  | 120 min | 677.2 | 6.7 | 107.7 |
| Comparative Example 4 | Blank | 928.8 | — | — |
|  | 30 min | 885.5 | 1.4 | 14.2 |
|  | 60 min | 832.9 | 3.2 | 38.1 |
|  | 90 min | 783.1 | 6.1 | 58.5 |
|  | 120 min | 733.6 | 5.9 | 80.0 |

From the results of the brief comparison of the above Examples with the Comparative Examples, it is found that low amount of metal impurities contained in the aqueous reaction medium for the hydroxylamine synthesis reaction could significantly promote the selection rate of the hydroxylamine production. In particular, the Fe metal impurity should be below 100 ppm.

On the other hand, in the context of catalytic activity, the catalytic activity increases and then decreases, as the Fe content decreases.

The above examples only exemplify the principles and the effects of the present invention. They are not used to limit this invention. It is possible for those skilled in the art to modify and or alter the above examples for carrying out this invention without contravening its spirit and scope. Therefore, the protection scope of this invention should be indicated as stated by the following claims.

What is claimed is:

1. A method for manufacturing hydroxylamine, comprising the steps of:
    pretreating an aqueous reaction medium taken from an oximation reaction of a hydroxylamine-oxime cycling process to reduce the amount of Fe metal in the aqueous medium to between 10 to 100 ppm, wherein the aqueous reaction medium comprises an acidic buffer agent, nitrate ions and metal impurities;
    introducing the aqueous reaction medium into a hydroxylamine synthesis reactor; and
    reducing the nitrate ions to the hydroxylamine in the presence of a catalyst in the aqueous reaction medium.

2. The method for manufacturing hydroxylamine according to claim 1, wherein, by the step of pretreating, the amount of Fe metal in the aqueous reaction medium is reduced to between 10 to 75 ppm.

3. The method for manufacturing hydroxylamine according to claim 2, wherein, by the step of pretreating, the amount of Fe metal in the aqueous reaction medium is reduced to between 15 to 55 ppm.

4. The method for manufacturing hydroxylamine according to claim 3, wherein, by the step of pretreating, the amount of Fe metal in the aqueous reaction medium is reduced to between 15 to 50 ppm.

5. The method for manufacturing hydroxylamine according to claim 4, wherein, by the step of pretreating, the amount of Fe metal in the aqueous reaction medium is reduced to between 15 to 30 ppm.

6. The method for manufacturing hydroxylamine according to claim 1, wherein the acidic buffer agent is selected from the group consisting of sulfuric acid, phosphoric acid and salts thereof.

7. The method for manufacturing hydroxylamine according to claim 6, wherein the acidic buffer agent is phosphate.

8. The method for manufacturing hydroxylamine according to claim 1, wherein the step of reducing the nitrate ions to the hydroxylamine is carried out at a temperature of from 20 to 100° C.

9. The method for manufacturing hydroxylamine according to claim 1, wherein the step of reducing the nitrate ions to the hydroxylamine is carried out at a pressure of from 10 to 30 kg/cm$^2$.

10. The method for manufacturing hydroxylamine according to claim 1, wherein the step of reducing the nitrate ions to the hydroxylamine is carried out at a pH of from 0.5 to 6.

11. The method for manufacturing hydroxylamine according to claim 1, wherein the catalyst is selected from the group consisting of Pd and Pd—Pt noble metals.

* * * * *